(12) United States Patent
Wieters et al.

(10) Patent No.: US 9,385,580 B2
(45) Date of Patent: Jul. 5, 2016

(54) ELECTROMAGNETIC ACTUATOR FOR A SURGICAL INSTRUMENT

(75) Inventors: Martin Wieters, Hamburg (DE); Marco Feldmann, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 363 days.

(21) Appl. No.: 13/808,387

(22) PCT Filed: Apr. 6, 2011

(86) PCT No.: PCT/EP2011/001699
§ 371 (c)(1),
(2), (4) Date: Apr. 18, 2013

(87) PCT Pub. No.: WO2012/003897
PCT Pub. Date: Jan. 12, 2012

(65) Prior Publication Data
US 2013/0193778 A1    Aug. 1, 2013

(30) Foreign Application Priority Data

Jul. 5, 2010   (DE) .......................... 10 2010 030 919

(51) Int. Cl.
| H02K 41/02 | (2006.01) |
| H02K 41/00 | (2006.01) |
| H02K 33/00 | (2006.01) |
| H01F 7/122 | (2006.01) |
| A61B 17/00 | (2006.01) |
| A61B 1/00  | (2006.01) |
| G02B 7/10  | (2006.01) |
| G02B 23/24 | (2006.01) |
| H01F 7/16  | (2006.01) |

(52) U.S. Cl.
CPC ............ *H02K 41/02* (2013.01); *A61B 1/00133* (2013.01); *A61B 1/00183* (2013.01);
(Continued)

(58) Field of Classification Search
CPC ....... H02K 41/00; H02K 33/00; H02K 41/02; H01F 7/122; H01F 7/1615; A61B 1/00188; A61B 1/00183; A61B 1/00133; A61B 17/00; A61B 2017/00398; A61B 2017/00876; G01B 23/2407; G02B 7/102
USPC ................ 310/12.01, 15, 12.04, 12.14, 12.15
See application file for complete search history.

(56) References Cited

U.S. PATENT DOCUMENTS 3,070,730 A * 12/1962 Gray ..................... H01F 7/1615
                                                          335/229
3,103,603 A *  9/1963 Reutter .................. H02K 33/06
                                                              310/15
(Continued)

FOREIGN PATENT DOCUMENTS

DE        1 253 407        11/1963
DE     37 17 872 A1        12/1988
(Continued)

OTHER PUBLICATIONS

International Search Report dated Jul. 29, 2011 issued in PCT/EP2011/001699.
(Continued)

*Primary Examiner* — Terrance Kenerly
*Assistant Examiner* — Alexander Singh
(74) *Attorney, Agent, or Firm* — Scully, Scott, Murphy & Presser, P.C.

(57) ABSTRACT

The invention relates to an electromagnetic actuator for a surgical or medical instrument, the actuator having a stator (19) and a displaceable element (10), which at least partially comprises a paramagnetic or ferromagnetic material and can be displaced from a first position into a second position by applying an electromagnetic field.
The invention is characterized in that the displaceable element (10) is or will be held in the first or in the second position by a permanent magnet.

5 Claims, 2 Drawing Sheets

Figure 1:
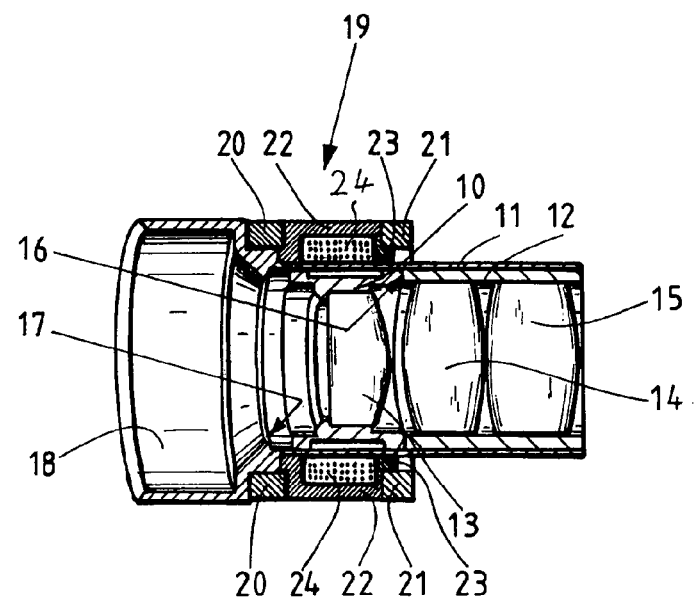

(52) U.S. Cl.
CPC ............. *A61B1/00188* (2013.01); *A61B 17/00* (2013.01); *G02B 7/102* (2013.01); *G02B 23/2407* (2013.01); *H01F 7/122* (2013.01); *H01F 7/1615* (2013.01); *H02K 33/00* (2013.01); *H02K 41/00* (2013.01); *A61B 2017/00398* (2013.01); *A61B 2017/00876* (2013.01)

(56) References Cited

U.S. PATENT DOCUMENTS

| | | | |
|---|---|---|---|
| 4,785,210 A | 11/1988 | Maruyama et al. | |
| 5,351,934 A * | 10/1994 | Jensen | F16K 1/123 251/129.1 |
| 6,246,131 B1 * | 6/2001 | Sheng | 310/12.24 |
| 6,265,956 B1 * | 7/2001 | Cascolan et al. | 335/234 |
| 7,476,990 B2 * | 1/2009 | Nakagawa et al. | 310/15 |
| 7,751,134 B2 * | 7/2010 | Sata et al. | 359/824 |
| 2010/0127580 A1 * | 5/2010 | Schrader | 310/12.26 |

FOREIGN PATENT DOCUMENTS

| | | |
|---|---|---|
| DE | 196 18 355 A1 | 11/1997 |
| DE | 200 00 397 U1 | 4/2000 |
| EP | 2 175 458 A2 | 4/2010 |

OTHER PUBLICATIONS

Chinese Office Action with Search Report dated Dec. 3, 2014 from related Chinese Application No. 201180033116.X, together with an English language translation.

* cited by examiner

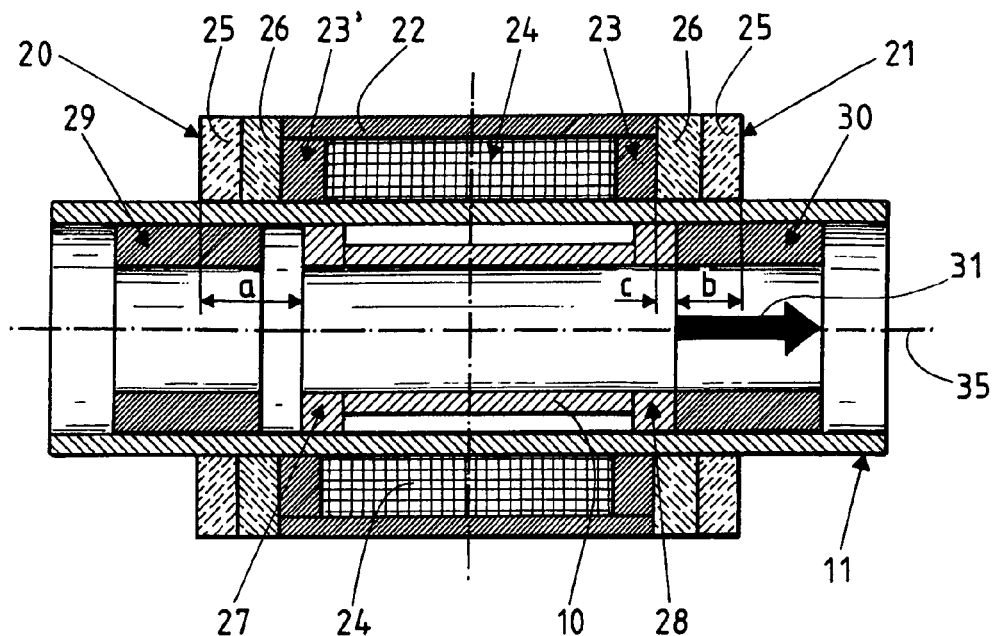
Fig. 3
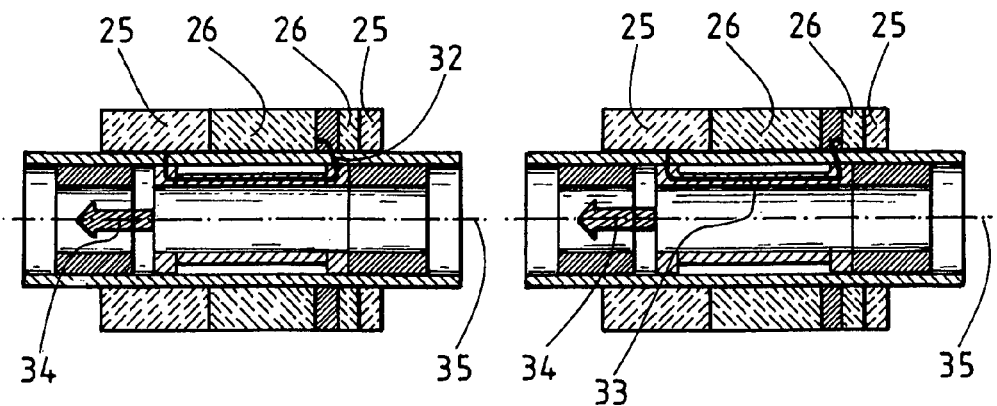
Fig. 4                    Fig. 5

ELECTROMAGNETIC ACTUATOR FOR A SURGICAL INSTRUMENT

CROSS-REFERENCE TO RELATED APPLICATIONS

This application claims priority to PCT Application EP2011/001699 filed on Apr. 6, 2011, which claims priority to Application No. DE 10 2010 030 919.2 filed on Jul. 5, 2010, the contents of each of which are incorporated herein by reference.

The invention relates to an electromagnetic actuator for a surgical or medical instrument, particularly an endoscope, the actuator having a stator and a displaceable element, which at least partially has a paramagnetic and/or ferromagnetic material and can be displaced from a first position into a second position by applying an electromagnetic field.

The document DE 196 18 355 C2 discloses an endoscope with a distally disposed objective, the image of which is transferred by an image transmitter to the proximal end, and which has at least one optical element such as a lens group, which is displaceable in the direction of the optical axis for focusing and/or changing the focal distance using a microdrive, the microdrive having at least one rotationally symmetric, axially movable sleeve, which surrounds and houses the lenses, or respectively the optical element of the movable lens group, and wherein the sleeve is composed of a permanently magnetic material and is movable in a magnetic field that is generated by a coil arrangement. In order to move and hold the sleeve, a permanent, electromagnetic field is generated.

The document DE 1 253 407 B discloses an endoscope with a distal emitting illuminating device for a body cavity part to be observed and an image transmitter, by which the illuminated image is recorded using an objective that can be adjusted in the axial direction and is supplied to an ocular or a camera, the objective being adjustable by an electromagnetic influence of an objective mount serving as an armature, from one setting into another setting with respect to the distal end of an image transmitter for at least two image sharpness settings. Here, at least one of the two settings is caused by a permanently applied electromagnetic field, and the other setting is brought about by the effect of a spring.

The object of the present invention is to specify an electromagnetic actuator by means of which it is possible to hold the displaceable element without power in defined positions, wherein the displaceable element of the actuator is to be displaced at low power.

This object is achieved by the subject matter of claim 1. Further developments of the invention are the subject matter of the dependent claims.

The object is achieved by an electromagnetic actuator for a surgical or medical instrument, particularly an endoscope, the actuator having a stator and a displaceable element, which at least partially has a paramagnetic and/or ferromagnetic material and is displaceable from a first position into a second position by applying an electromagnetic field, wherein the displaceable element is, or will be, held in the first position by a permanent magnetic field and after displacement into the second position, is, or will be, held in the second position by a permanent magnetic field.

By using a permanent magnetic field it is possible to hold the displaceable element without power, particularly subsequently, in the first position as well as the second position, so that no additional power must be introduced into the system.

Particularly preferably is an embodiment, in which the stator comprises two permanent magnets that are poled to repel each other. Within the scope of the invention, poled to repel each other means in particular that the poles of the two permanent magnets disposed towards each other repel, that is, the same poles are adjacent to each other. As a result of this, it is particularly simple for the displaceable element to be held without power in the first and/or the second position. Here, the displaceable element preferably does not comprise a permanent magnet, but rather is composed exclusively of a paramagnetic and/or a ferromagnetic material and possibly additionally of a non-magnetic material, the ferromagnetic material being preferred due to the greater effect of intensifying the magnetic field.

For generating the electromagnetic field, preferably a coil is provided that is preferably disposed between the permanent magnets. Using this arrangement it is possible to displace the displaceable element even with a relatively weak electromagnetic field. During displacement, or respectively switching, of the electromagnetic actuator, the permanent magnetic field of the two permanent magnets and the electromagnetic field of the coil interact. As a result of this, it is possible that the permanent magnets are not demagnetized by the electromagnetic field.

Preferably two stops are provided which define the first and the second position. Due to the stops, the displaceable element can move into corresponding end positions or intermediate positions, beyond which the displaceable element cannot move. Upon contact of the displaceable element against a stop, a force preferably acts, particularly non-dissipating, on the displaceable element in the direction of the stop. In doing so, the displaceable element is preferably pulled in the direction of a metastable position, which the displaceable element, however, cannot completely reach due to the stops. A magnetic force acts in the respective positions, thus in the first position in the case in which the displaceable element lies in the first position, and also in the case in which the displaceable element lies in the second position, in the direction of the respective stop so that the displaceable element is held defined at the stop. A well-defined position results from this.

Instead of stops, it would also be possible to not provide a stop, and to enable a first, or respectively second position in the region of an energy minimum of the interaction of the permanent magnetic field through the permanent magnets and of the material of the displaceable element. The variant with the stops is, however, significantly preferred due to the defined positions.

If a paramagnetic and/or ferromagnetic material is disposed between the permanent magnets of the stator, particularly low power is sufficient for the electromagnetic field in order to enable a displacement of the displaceable element from a first position into the second position or vice versa. Here, the paramagnetic and/or ferromagnetic material is particularly part of the stator.

Preferably the coil is enclosed towards the outside by the permanent magnets and the paramagnetic and/or ferromagnetic material, particularly of the stator.

Due to the arrangement of a paramagnetic and/or ferromagnetic material, both in the displaceable element as well as in the stator, a soft magnetic return path is created for the coil, whereby strong magnetic fields and with it high power densities can be achieved already at low currents through the coil.

Preferably the displaceable element is mounted longitudinally axially displaceable in a tube. The longitudinally axially displacement is along the longitudinal axis of the tube. Preferably the tube is cylindrical. It is preferable to generate a magnetic field that is symmetrical about the longitudinal axis, particularly rotationally symmetrical. As a result, and in particular due to the measure that the displaceable element, the coil and the permanent magnets are ring shaped in section, and specifically in the section transverse to the longitudinal axis, uniform forces act on the displaceable element so that a displacement is possible at low power. A brief electrical switching impulse of less than 100 milliseconds and less than 500 milliamperes through the coil is sufficient for the displacement process of the displaceable element, or respectively the switching process from a first position into a second position, or vice versa.

Preferably a surgical or medical instrument, particularly an endoscope is provided with an electromagnetic actuator according to the invention.

Figure 2:
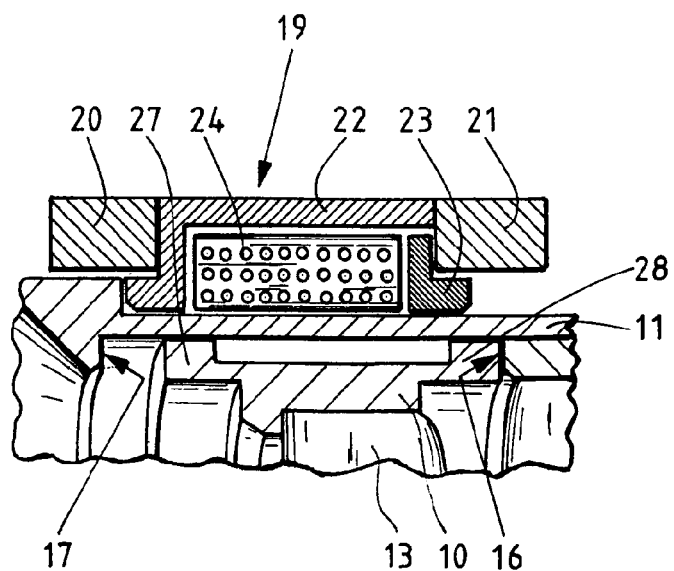

The invention is described below, without restricting the general intent of the invention, based on exemplary embodiments in reference to the drawings, whereby we expressly refer to the drawings with regard to the disclosure of all details according to the invention that are not explained in greater detail in the text. In the figures:

FIG. 1 shows a schematic three-dimensional sectional representation through a part of an endoscope having an actuator according to the invention, FIG. 2 shows a schematic enlarged section from FIG. 1, FIG. 3 shows a schematic sectional representation of another embodiment of an actuator according to the invention, FIG. 4 shows a schematic sectional representation of the embodiment from FIG. 3 with a schematic flux representation, and FIG. 5 shows a schematic sectional representation of the embodiment from FIG. 3 with a schematic flux representation.

In the following figures, the same or similar types of elements or respectively corresponding parts are provided with the same reference numbers so that a corresponding re-introduction can be omitted.

FIG. 1 shows a schematic three-dimensional sectional representation through a part of an endoscope having an actuator according to the invention. The actuator can be disposed in a shaft of the endoscope, not shown. The shaft of the endoscope would be disposed coaxially about the actuator in FIG. 1, specifically coaxially with a diameter that is somewhat larger than the outer diameter of the distal end 18 of the guide tube 11.

The guide tube 11, which can be composed of a metal or plastic, wherein in this case it is important that tube is composed of a non-magnetic material, serves as a radial guidance of the displaceable element 10. The displaceable element 10 can have a lens 13 for example, which is a component of an objective that in addition has lenses 14 and 15, which are inserted in a fixed retaining element 12 and are appropriately held. The fixed retaining element 12 is fixed, or respectively attached, in the guide tube 11 and defines a stop 16. The further stop 17 towards the distal end is also defined by the guide tube 11 by a collar toward the inside. This exemplary embodiment according to FIG. 1 is a rotationally symmetric design in which an axially displaceable element 10 is provided. The displaceable element 10 can be pushed from a proximal position, as represented in FIG. 1, toward the left in FIG. 1 to a stop 17 into a distal position. The displaceable element 10 is designed as a type of sleeve, which particularly is composed of a soft magnetic material, for instance a ferromagnetic material, or respectively has this material.

In addition to the ferromagnetic and/or paramagnetic material, the displaceable element 10 can also have a friction reducing coating on the surface that is disposed toward the interior wall of the guide tube 11.

FIG. 2 shows an enlarged section of FIG. 1, in which the shape of the respective elements can be seen more clearly.

The displaceable element 10 has a distal pole shoe 27 and a proximal pole shoe 28. These interact with the magnetic field and the permanent magnets 20 and 21, which are designed as rings and are disposed rotationally symmetrical about the longitudinal axis of the electromagnetic actuator. A first intermediate part 22 and a second intermediate part 23, composed of paramagnetic or ferromagnetic material, are provided between the permanent magnets 20 and 21, and are designed also having pole shoes or as pole shoes. The first intermediate part 22 and the second intermediate part 23 can also be formed integrally thus forming a single intermediate part. Further, a coil 24 is provided that is enclosed toward the outside by the first intermediate part 22 and the second intermediate part 23, and is surrounded toward the inside also by paramagnetic and/or ferromagnetic material of the displaceable element 10, except for the interruption by the guide tube 11. As a result, a very strong amplification of the electromagnetic field is attained. The stator 19 of the electromagnetic actuator is composed substantially of the two permanent magnets 20 and 21, the two intermediate parts 22 and 23, and the coil 24.

The material of which the displaceable element 10 is composed or respectively has, can be St37 or C45k for example. The outer contour of the displaceable element represents a double armature. Thereby, there are two pole shoes, namely a distal pole shoe 27 and a proximal pole shoe 28. The outsides of the pole shoes further serve as sliding surfaces for the sliding pairing between the guide tube 11 and the displaceable element 10. The interior contour of the displaceable element is preferably axially symmetrical. However, within certain boundaries there can be deviations from the symmetry in order to integrate a shoulder for installation of a lens 13 for example. The displaceable element is preferably matt black.

The stator 19 substantially comprises two homogeneous permanent magnets which have the same material, or respectively the same magnet and magnetization strength, and correspondingly the same dimensions. Furthermore, a coil 24 is provided and two ferromagnetic components, or respectively intermediate parts 22 and 23, which serve as magnetic flux guides for reinforcing and focusing of magnetic fields. The intermediate parts 22 and 23 are implemented shaped like horse shoes in a section longitudinally axially through the stator and in a pole shoe-like symmetrical design. Both the displaceable element 10 and the stator 19 are preferably built axially symmetric. The permanent magnets 20 and 21 are mounted poled repelling each other, or set up, respectively.

The electromagnetic actuator can be present in four different states. The first state is the state represented in FIGS. 1 and 2, in which the displaceable element 10 is located in the stable proximal position. Here, the resulting force of the permanent magnets acts on the displaceable element against the proximal stop 16. Furthermore, the displaceable element can be located in a stable distal position, which is not represented in FIGS. 1 and 2. The resulting force of the permanent magnets then acts on the displaceable element 10 against the distal stop 17.

The third state is that the actuator moves the displaceable element out of the distal position. The resulting force of the coil and the permanent magnets then moves the displaceable element 10 in the proximal direction. Conversely, the fourth state is defined in which the actuator moves the displaceable element 10 out of the proximal position. Here, the resulting force of the coil and the permanent magnets is such that the displaceable element 10 is pushed in the distal direction.

This functioning is described in more detail in the following.

The FIGS. 3 to 5 show schematic sectional representations through an electromagnetic actuator, the respective elements and features being indicated schematically. In FIG. 3 the coil 24 is without current, that is, the coil does not generate a magnetic field. The stator comprises, corresponding as in FIGS. 1 and 2, intermediate parts 22, 23 and 23', composed of a ferromagnetic material, which are designed horseshoe-shaped in section. The intermediate parts 22, 23 and 23' can be manufactured as a common piece, thus integrally.

A magnetic south pole is schematically indicated with 25, and a magnetic north pole is schematically indicated with 26. A first intermediate part, or respectively component, is indicated with 22, and, in each case, a second intermediate part, or respectively component, which is designed as a pole shoe, is indicated with 23 and 23'. Correspondingly, the elements 10, 27 and 28, which represent the ferromagnetic parts of the displaceable element 10, can also be integral. The distal pole shoe is indicated with 27, and the proximal pole shoe is indicated with 28.

In this case, the retaining forces of the displaceable element are only generated by a permanent magnetic field of the two permanent magnets. Due to the arrangement of the magnets 20 and 21, the same magnetic pole is located at both pole shoes 23 and 23' of the stator. The magnetic flux tries to flow along the path of least magnetic resistance. In relation to air, the magnetic resistance of the ferromagnetic material used is much lower, so that the system overall attempts to minimize the air gap. This is called reluctance. Hereby, the pole shoes which are preferably composed of soft magnetic, or respectively ferromagnetic material, are overlapped whereby a movement, or respectively a force results.

In order to attain a retaining force in the proximal direction, as indicated in FIG. 3 by the force 31, towards the proximal stop element 30, the following conditions should be given. The proximal pole shoe 28 of the displaceable element 10 must be positioned closer with respect to the proximal end of the proximal permanent magnet 21 than the distal pole shoe 27 of the displaceable element with respect to the distal end of the distal permanent magnet 20. Thus, a must be greater than b. In addition, the proximal pole shoe 28 of the displaceable element 10 must extend proximally beyond the proximal pole shoe 23 of the armature. That is, c must be greater than zero. If c=0, the system would be in a magnetic, or respectively energy, minimum. Then, there would no longer be a resulting force 31. A corresponding force in the direction of the energy minimum would only arise with a displacement out of this position. This would lead to a non-discrete positioning, which is why the embodiment with corresponding stops is preferred.

The displaceable element 10 forms the magnetic return path for the two magnets 20 and 21 so that the lowest magnetic resistance, or respectively the most favorable energy state of the system, can be attained using the displaceable element 10. Depending on the position of the displaceable element, thus also depending on the position of the stop elements 29, or respectively 30, different retaining forces can be realized. In the example shown, the electromagnetic actuator is designed so that the position of the displaceable element 10 at the stop, thus for example at the proximal stop element 30, does not correspond to the most favorable energy state. Thereby, the electromagnetic actuator further attempts to pull the displaceable element into the position of the lowest resistance, whereby the resulting retaining force (reluctance) arises.

Now, in order to move the displaceable element 10 from the proximal position into the distal position, the coil 24 is energized. As a result, a total magnetic field can be generated, which generates a force in the distal direction that is greater than the retaining force in the proximal direction. This is shown in FIGS. 4 and 5. The force in the distal direction is called the displacement force 34. By energizing the coil 24, a corresponding magnetic field results from the summation of the magnetic field of the distal permanent magnet 20 and the coil, which is schematically indicated by a magnetic north pole 26 and a magnetic south pole 25 on the left side of FIG. 4 and FIG. 5. In the ideal case, the coil generates a magnetic flux which corresponds to the flux of the distal permanent magnet 20. Thereby the magnetic field is reinforced toward the proximal second intermediate part 23, or respectively the stator pole shoe. The distal permanent magnet 20 and the coil, viewed abstractly, form a large contiguous magnet that schematically has greater, ideally double, field strength than the proximal permanent magnet 21. As a result of this, corresponding magnetic fluxes 32 and 33 arise, which are indicated in FIGS. 4 and 5, and a corresponding displacement force 34 arises toward the distal end. Due to the interaction of the three magnetic components (two permanent magnets 20 and 21 and the coil 24) the displaceable element 10 is moved out of its proximal position into its distal position.

Using the represented design, it is no longer necessary that the magnetic flux of the coil completely cancels the magnetic flux of the permanent magnet. As a result, the danger that the magnetic field of the coil demagnetizes the permanent magnets is reduced. By surrounding the coil with a ferromagnetic material a very high degree of efficiency can be attained. This minimizes the necessary switching current, and thus possibly arising heat, which should be avoided in the distal region of an endoscope.

The electromagnetic actuator is preferably used with endoscopes that have an optical system. In particular, a lens can be displaced by the electromagnetic actuator so that the lens can be displaced axially longitudinally along the longitudinal axis 35. As a result it is possible to focus, or displace the focal distance of the objective. A mirror can also be provided, instead of or in addition to the lens, by means of which the viewing direction in the distal region of an endoscope can be changed for an operator. Due to the solution according to the invention, a less expensive design with lower space requirements can be realized so that the lumen, available to the lenses for example, is only slightly reduced, such that objectives with high luminosity, and thus endoscopes with high luminosity can be implemented.

All named features, including those to be taken from the drawings alone, and individual features, which are disclosed in combination with other features, are considered individually and in combination as essential to the invention. Embodiments according to the invention can be fulfilled through individual features or a combination of several features.

LIST OF REFERENCE SYMBOLS 10 displaceable element
11 guide tube
12 fixed retaining element
13 lens
14 lens
15 lens
16 stop
17 stop
18 distal end
19 stator
20 permanent magnet
21 permanent magnet
22 first intermediate part
23, 23' second intermediate part 24 coil
25 magnetic south pole
26 magnetic north pole
27 distal pole shoe
28 proximal pole shoe
29 distal stop element
30 proximal stop element
31 force
32 magnetic flux
33 magnetic flux
34 displacement force
35 longitudinal axis
a distance
b distance
c distance

The invention claimed is:

1. An electromagnetic actuator for a surgical or medical instrument, the actuator comprising:
    a stator, the stator comprising two permanent magnets which are poled repelling each other;
    a displaceable element which at least partially has a ferromagnetic material and can be displaced from a first position into a second position by applying an electromagnetic field, the displaceable element having a hollow interior between a proximal opening and a distal opening,
    at least one optic lens disposed in the hollow interior,
    two stops which define the first and the second position; and
    a ferromagnetic material disposed between the two permanent magnets of the stator, the ferromagnetic material having a concavity; and
    a tube, wherein the displaceable element is disposed in the tube so as to be movable in a longitudinal direction of the tube;
    wherein the displaceable element is or will be held in the first position by a permanent magnetic field and after displacement into the second position is or will be held in the second position by a permanent magnetic field;
    a coil is provided for generating the electromagnetic field, the coil being disposed in the concavity of the ferromagnetic material;
    upon contact of the displaceable element at one of the two stops, a force acts on the displaceable element in the direction of the one of the two stops;
    the coil is enclosed toward the outside by the permanent magnets and the ferromagnetic material; and
    the displaceable element having a distal pole shoe and a proximal pole shoe to define a concavity on an exterior surface of the displaceable element,
    wherein an outside of the distal pole shoe and an outside of the proximal pole shoe serve as sliding surfaces for a sliding contact between the tube and the displaceable element; and
    the ferromagnetic material having first and second side walls and a bottom forming a concavity, the first and second side walls each extending in a flange along the longitudinal direction to form a distal flange and a proximal flange, wherein the distal flange opposes the distal pole shoe and the proximal flange opposes the proximal pole shoe for at least the portion of a range of motion of a distal and proximal pole shoes in the longitudinal direction.

2. The electromagnetic actuator according to claim 1, wherein the coil is disposed between the two permanent magnets.

3. The electromagnetic actuator according to claim 1, wherein the displaceable element, the coil and the permanent magnets are ring-shaped in section.

4. A surgical or medical instrument having an electromagnetic actuator according to claim 1.

5. The electromagnetic actuator according to claim 1, wherein each of the flanges is disposed in a gap between the tube and an individual permanent magnet of the two permanent magnets.

* * * * *